United States Patent [19]
Ellis et al.

[11] Patent Number: 5,476,692
[45] Date of Patent: Dec. 19, 1995

[54] METHOD OF STRENGTHENING GLASS

[75] Inventors: Bryan Ellis; Xiao M. Chen; Angela B. Seddon, all of Sheffield, England

[73] Assignee: British Technology Group Ltd, London, England

[21] Appl. No.: 142,432

[22] PCT Filed: May 20, 1992

[86] PCT No.: PCT/GB92/00913

§ 371 Date: May 6, 1994

§ 102(e) Date: May 6, 1994

[87] PCT Pub. No.: WO92/20633

PCT Pub. Date: Nov. 26, 1992

[30] Foreign Application Priority Data

May 24, 1991 [GB] United Kingdom .................. 9111261

[51] Int. Cl.$^6$ ..................................................... B05D 3/06
[52] U.S. Cl. ......................... 427/558; 427/386; 427/387; 427/389.7
[58] Field of Search ............................. 215/12.2, DIG. 6; 427/389.7, 386, 387, 558; 428/34.7

[56] References Cited

U.S. PATENT DOCUMENTS

| | | | |
|---|---|---|---|
| 4,056,208 | 11/1977 | Prejean | 427/386 X |
| 4,250,068 | 2/1981 | Ali-Zaidi | 428/426 X |
| 4,374,879 | 2/1983 | Roberts et al. | 524/276 X |

FOREIGN PATENT DOCUMENTS

| | | |
|---|---|---|
| 1526988 | 4/1988 | Australia . |
| 0250779 | 1/1988 | European Pat. Off. . |
| 0289325 | 11/1988 | European Pat. Off. . |

OTHER PUBLICATIONS

World patents Index Latest, Accession No. 90–372481, Week 50, Derwent Publications Ltd. London, GB; & JP, A, 2269780 (Kansai Paint KK) 05, Nov. 1990, see abstract.

*Primary Examiner*—Michael Lusignan
*Attorney, Agent, or Firm*—Cushman, Darby & Cushman

[57] ABSTRACT

A method of strengthening glass using a mixture of a silane and a resin, the mixture being applied to the glass surface as an aqueous emulsion which is then cured. The silane is a reaction product of a silane coupling agent, which contains an epoxy group, with an unsaturated carboxylic acid, and the resin is a resin having at least two polymerisable unsaturated groups in the molecule. Preferably the silane and the resin have unsaturated reactive groups of matched reactivity. Advantageously the mixture contains about 20 parts of the silane per hundred parts of the resin. In another embodiment a silane coupling agent is dissolved in a polymerisable resin, the mixture of silane and resin is emulsified in water, the emulsion being applied as a coating, which is then cured.

40 Claims, No Drawings

METHOD OF STRENGTHENING GLASS

The present invention relates to a method of strengthening glass by applying a coating to a surface of the glass. The method of the present invention has particular application in the strengthening of glass containers.

A method of increasing the pressure-resistant strength and impact strength of a glass container has been proposed in published Australian Patent Application No. 15269/88. In the method of the Australian Patent Application a silane coupling agent is used in conjunction with a reactive compound having at least two (meth)-acryloyl groups in the molecule and capable of being polymerised by irradiation. The silane coupling agent is an organosilicon monomer having at least two different reactive groups in the molecule, one reactive group being capable of reacting with glass, and another reactive group being capable of reacting with the (meth)acryloyl groups.

In the said Australian Patent Application the reactive compound may be applied in a separate step after the surface of the glass container has been treated with the silane coupling agent or a mixture of the silane coupling agent and the reactive compound may be applied to the surface of the glass container in a single operation. In either case the reactive compound is applied in solution in an organic solvent, preferably methylethylketone.

Organic solvents such as methylethylketone require substantial precautions to be taken when used in an industrial process, for example there is a great need for fire precautions and a need to prevent the solvent escaping into the atmosphere. It is accordingly an object of the present invention to provide a method of strengthening glass, particularly glass containers, which does not involve the use of organic solvents.

According to the present invention there is provided a method of strengthening glass by applying a coating of a mixture of a silane and a resin containing at least two polymerisable unsaturated groups in the molecule to a surface of the glass and then curing the coating, wherein the silane is a reaction product of a silane coupling agent, which contains an epoxy group, with an unsaturated carboxylic acid, and the mixture of the silane and the resin is applied to the surface of the glass as an aqueous emulsion.

It has not previously been considered practicable to strengthen a glass container by application of a coating including a silane compound in an aqueous suspension because the silane gels on contact with water. In accordance with the present invention, however, the mixture comprising the resin and the reaction product of the silane coupling agent, which included an epoxy group, with the unsaturated carboxylic acid yields an aqueous coating mixture having a pH in a range at which the silane is stable in the presence of water and does not gel. The reaction product of the silane coupling agent with the unsaturated carboxylic acid may be stored and made up into a mixture for use in accordance with the present invention at a later date.

The reaction of the silane coupling agent with the unsaturated carboxylic acid also has the feature of introducing a double bond into the silane, thereby facilitating co-polymerisation between the silane and the resin to produce a strong coating on the surface of the glass.

Conveniently the silane coupling agent contains the epoxy group as a substituent in an organofunctional group, that is to say a reactive group which includes linked carbon atoms but may also include other atoms, for example oxygen or nitrogen atoms, linked with the carbon atoms. The organofunctional group may include a cyclic group.

Preferably the epoxy group is a substituent in an organofunctional group which comprises an alkyl chain having an ether linkage within the chain.

The silane coupling agent is advantageously a trialkoxyl silane having an alkyl chain including an ether linkage within the chain and the alkyl chain containing a substituent epoxy group. Preferably the substituent epoxy group is a terminal epoxy group. Such preferred silane coupling agents are of the general formula

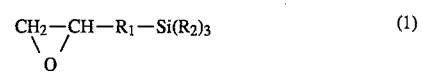

where $R_1$ is an organofunctional group and $R_2$ is alkoxyl.

Examples of preferred silane coupling agents which may be used in a method according to the present invention to react with an unsaturated carboxylic acid to give the silane compound of the mixture are

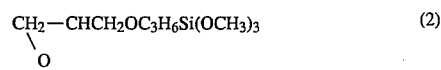

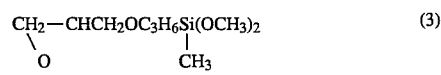

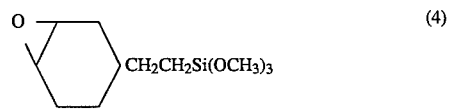

The epoxy organofunctional alkoxyl silanes exemplified above can be reacted in accordance with the present invention with an unsaturated carboxylic acid to form the silane which is a component of the mixture. Preferably the silane used in a method according to the present invention is a reaction product of an epoxy trialkoxyl silane with an acid of the acrylic acid series, ie an acid of the formula

where $R_3$ is hydrogen or an alkyl group, hereinafter referred to as "an acrylic acid". Preferably the acid is either acrylic acid itself or methacrylic acid.

The silane may be a reaction product of the silane coupling agent with an unsaturated dibasic acid. The silane may further be a reaction product of the silane coupling agent with a mixture of different unsaturated carboxylic acids.

The reaction between the epoxy trialkoxyl silane and the acid is advantageously effected with at least a stoichiometric quantity of the acid. When an acrylic acid is used, the reaction product may be described as an epoxy acrylate silane. In a mixture with the resin, the epoxy acrylate silane is stable in the presence of water so that gelling of the silane does not take place simply on contact with water. The epoxy acrylate silane product can be stored without gelling and used at a desired later time.

When a silane coupling agent of formula (1) above is reacted with an acrylic acid of formula (5), the silane component of the mixture has the formula

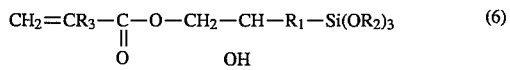

where $R_1$, $R_2$ and $R_3$ are as above.

Preferably the resin which is used in the mixture according to the present invention is a reaction product of an epoxy resin with an unsaturated carboxylic acid, for example a dibasic acid or an acid of the formula

 (5)

where $R_3$ is hydrogen or an alkyl group.

Within this group the preferred resins for use in the present invention are epoxy modified acrylates or methacrylates obtained by esterifying the epoxy groups of epoxy resins with either acrylic acid or methacrylic acid. Advantageously the epoxy acrylate resins used in the method of the present invention are derived from bisphenol-A, for example

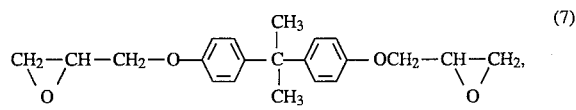 (7)

which is derived from bisphenol-A by reaction with epichlorhydrin, is reacted with an acrylic acid of formula (5) to give an epoxy acrylate resin of formula (8):

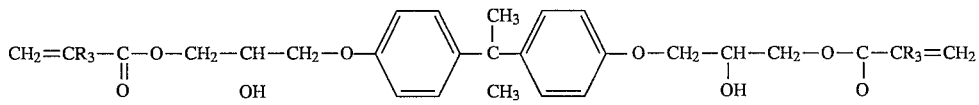

Epoxy acrylate resins of this general formula are obtainable commercially, for example Crodaplast UVE 100 which is a diacrylate of liquid bisphenol-A epoxy resin with a polymerisable acrylate diluent to modify the viscosity of the resin, and which is obtainable from Croda Resins Limited.

The epoxy resin of Formula (7) is the simplest epoxy resin based on bisphenol-A, and there may be advantage in using an epoxy resin based on bisphenol-A and having a slightly higher molecular weight.

Fluorinated resins may also be used in accordance with the present invention and such fluorinated epoxy acrylate resins may, for example, be derived from

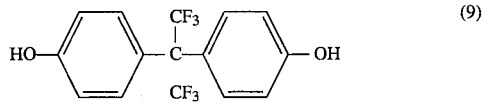 (9)

i.e. a fluorinated bisphenol-A.

Alternative resins which may be used in a method in accordance with the present invention are polyurethane acrylates or methacrylates, polyhydric acrylates or methacrylates, polyester acrylates or methacrylates and polyether acrylates or methacrylates.

In accordance with a preferred feature of the present invention the mixture of silane and resin includes a silane and a resin which have unsaturated reactive groups of similar or matched reactivity. Such a mixture of silane and resin of matched reactivity is obtained for example when a silane of formula (6) is used with an epoxy acrylate resin of formula (8) and the radical $R_3$ is the same in both the silane of formula (6) and the resin of formula (8). Preferably the radical $R_3$ in both the silane and the resin is either hydrogen or a methyl group, resulting in the use of either acrylic acid in the formation of both the silane and the resin or the use of methacrylic acid in the formation of both the silane and the resin.

Silane and resin of matched reactivity may also be obtained by deriving both components of the mixture by reaction with an unsaturated dibasic acid such as maleic acid.

The use of a mixture comprising a silane and a resin of matched reactivity, and preferably containing at least 10 parts of the silane per 100 parts of the resin, has been found to give substantial improvements in the strengthening of a glass article. Increases in strength of up to 100% have been attained on glass rods, and glass containers have had their strength improved by as much as 50%. It is thought that the substantial improvements in glass strength obtained when using a silane and a resin of matched reactivity results because the similar reactivities of the reactive groups in the silane and the resin facilitate co-polymerisation between the silane and the resin so that there is cross-linking between the two interpenetrating networks formed by the polymerisation of the silane and the resin respectively, and a covalently coupled interpenetrating network is formed.

Preferably the matched reactivities of the silane and the resin are achieved, as in the examples mentioned above, by using the same terminal group on both the silane and the resin. However, in accordance with the present invention the reactive groups need not be terminal groups.

In the method of strengthening glass in accordance with the present invention the mixture of silane and resin advantageously includes a substantially larger proportion of silane than in the preferred range of coating mixtures proposed in prior Australian Application No. 15269/88. In accordance with the present invention the silane may, for example, be present in an amount from 5 to 40 parts per 100 parts of the resin but is preferably present in an amount from 15 to 30 parts per 100 parts of the resin. Most advantageously there are at least 20 parts of the silane per hundred parts of the resin.

When the mixture of silane and resin is formed into an aqueous emulsion with an emulsifier there may be from 100 to 600 parts by weight of the mixture to 1,000 parts of water.

When the aqueous emulsion of the mixture is being used to strengthen a glass container, the mixture to water ratio is selected to provide a suitable consistency of the emulsion for the particular method of application of the emulsion to the glass container. If the glass container is to be dipped in the aqueous emulsion, the emulsion may conveniently contain an amount of the order of 250 to 450 parts by weight of the mixture to a liter of water. Alternatively, if the aqueous emulsion of the mixture is to be applied to the glass container by spraying the outer surface of the glass container, the aqueous emulsion will conveniently contain an amount of the order of 150 to 200 parts by weight of the mixture to a liter of water.

All the examples of a method according to the present invention which will be described include a desirable feature that time is allowed for the water to evaporate from the applied emulsion and for the silane in the resin mixture to commence reaction with the surface of the glass before curing of the resin is commenced. There is often sufficient heat remaining in the container after applying the aqueous emulsion for these processes to take place during the inevitable delay in a practical process between application of the emulsion and the commencement of curing. However additional heat may be applied to speed them up.

Most advantageously the resin used is cured by irradiation with ultra-violet light and the mixture preferably includes a photo initiator to obtain a speedy cure of the mixture, for example in a time of the order of 15 seconds.

However, it is within the scope of the present invention for the resin to be heat cured, in which case the mixture additionally includes a free radical initiator which is sensitive to heat.

A method of strengthening glass in accordance with the present invention may use a mixture including a plurality of silanes, each of which is a reaction product of a silane coupling agent which contains a substituent epoxy group with an unsaturated carboxylic acid. More specifically, each of the silanes may be a reactive product of a trialkoxyl silane having an alkyl chain which includes an ether linkage and the alkyl chain contains a substituent epoxy group with an unsaturated carboxylic acid, for example the silane coupling agents may be a mixture of the silanes of formulae (2), (3) and (4).

According to a further feature of the present invention the glass surface to which the aqueous emulsion is applied is first exposed to contact with water vapour.

It has been found that, if the aqueous emulsion of a mixture in accordance with the present invention is applied to a damaged gllass surface immediately after the damage has been inflicted on the surface. the coated surface does not retain its improved strength for a substantial period. However, if the damaged surface is first treated with water, for example by steaming in an autoclave, and the surface is subsequently coated with an aqueous emulsion in accordance with the present invention, the coated surface retains its strength.

In the manufacture of glass containers it is thought that damage to a part of the glass surface occurs relatively early in the manufacture of the glass and in particular before the glass container is passed through the annealing lehr. In these circumstances it is probable that the exposure of the glass container to atmospheric water in the annealing lehr constitutes a sufficient treatment with water to ensure that the glass container, when subsequently coated with an aqueous emulsion of a mixture according to the present invention, will retain its strength throughout the useful life of the glass container. However, it is within the scope of the present invention for additional water vapour to be introduced into the annealing lehr to ensure that the surface of the glass container is adequately treated before application of the aqueous emulsion and the coated glass container does maintain its strength throughout the life of the glass container, despite subsequent moisture attack and mechanical abrasion.

In a preferred embodiment of the present invention the silane component of the mixture which is made into an aqueous emulsion is a reaction product of a trimethoxyl silane having an alkyl chain including a terminal epoxy group of the general formula

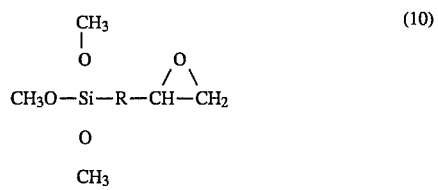 (10)

where R is an organofunctional group with acrylic acid

 (11)

in stoichiometric proportions to give the reaction product

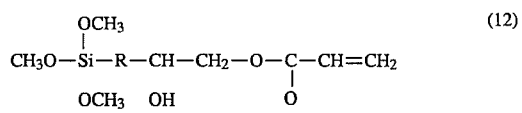 (12)

This reaction has a two-fold effect in accordance with the present invention. Firstly it creates a reacted silane coupling agent having a terminal double bond for cross-linking polymerisation with the resin, and secondly, when the reacted silane coupling agent is dissolved in the resin and emulsified, it yields an emulsion having a pH in the range of 3 to 4 which inhibits gelation of the silane.

There will now be described, by way of example, one method of making an aqueous emulsion according to the present invention for application to a glass surface to strengthen the glass.

The first step is the preparation of the reaction product of the silane coupling agent with the unsaturated carboxylic acid. In this preferred example 32 grams of γ-Glycidoxypropyltrimethoxysilane, obtainable for example from Dow Corning under the reference Z6040, were mixed with 9 grams of acrylic acid and heated to a temperature of 100° C. A catalyst such as benzyl triethyl ammonium chloride is then added and the mixture maintained at 100° C. for one hour to complete the reaction which is believed to be as follows:

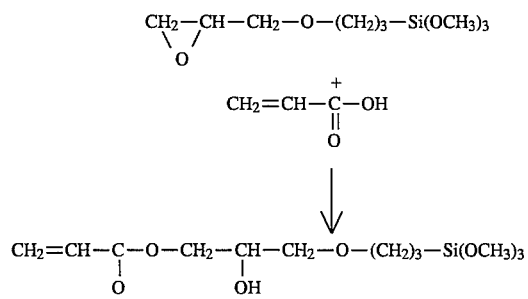

The product of the process described above will be referred to as "the reacted silane coupling agent" or "the reaction product".

Provided that the reacted silane coupling agent is kept dry, it is stable. The reacted silane coupling agent may therefore be stored in the dark for a period of two to three months or may be used immediately in a method according to the present invention as follows:

The reacted silane coupling agent was made specifically to match its unsaturated reactive groups with the unsaturated reactive groups of the selected resin, namely Crodaplast UVE 100 (obtainable from Croda Resins Limited), which is an epoxy acrylate resin of Formula (8) (in which $R_3$ is hydrogen) in a tripropylene glycol diacrylate diluent. The 41 grams of the reacted silane coupling agent are dissolved in 200 grams of the solution of epoxy acrylate resin, the resin being warmed to aid solution.

13.6 grams of a commercially available emulsifier, the surface active agent Antarox CO-880 obtainable from GAF, was dissolved in 1.1 liters of water. The mixture or solution of reacted silane coupling agent in the epoxy acrylate resin was cooled and then added to the water together with 10.6 grams of a commercially available photo initiator, Irgacure 651, and the mixture was stirred vigorously using a mechanical mixer. The pH of the emulsion as prepared is approximately 3 and the aqueous emulsion is stable.

The aqueous emulsion as described above is suitable for application to glass containers or other glass articles by spraying. When the aqueous emulsion is to be applied by a dipping process, less water is used-as little as half the quantity of water may be employed in preparing an aqueous emulsion for application by dipping.

The aqueous emulsion of the above example, at a temperature of 20° C.–30° C., has been applied to glass bottles at a temperature of 105° C. taken from production. After application of the aqueous emulsion, coated bottles were put in an oven at 160° C. for three minutes, and then irradiated by ultra violet radiation whilst still hot to produce a cured coating of about 5–8 micrometers thickness.

Examples will now be given of tests made on a number of samples of bottles in order to demonstrate the improvement in strength of glass bottles treated with an aqueous emulsion in accordance with the present invention. In all the following Examples the bottles were subjected to internal bursting pressure tests as tests of bottle strength, such tests being carried out on a ramp tester.

In all the following Examples the coated bottles were coated with the aqueous emulsion prepared as described above.

In each Example, all the samples of glass bottles used were taken from the same mould in order to avoid differences in bottle strength due to mould variations. All tests were carried out on newly-manufactured 275 ml beer bottles of amber soda-lime silica glass. All bottles had been treated at the hot end to produce a conventional tin oxide coating on the bottle. However, all bottles used in the following Examples were free of a cold end coating at the time of application of the aqueous emulsion, the bottles in each Example being at a temperature of 105° C. when the aqueous emulsion was applied.

After the aqueous emulsion coating in accordance with the present invention had been applied either by dipping or spraying as specified in the example, the coated bottles in each example were heated at 160° C. for three minutes prior to curing of the coating by ultra violet radiation. The heat treatment at 160° C. for three minutes caused evaporation of water from the applied aqueous emulsion and during this period initial reaction between the silane and the glass container commenced. This initial reaction of the silane is a "pre-reaction" in that it occurs before the free radical polymerisation of the resin and the silane as a result of the ultra violet irradiation cure.

In Examples 1 and 2, in order to simulate production conditions, the glass bottles were taken from the lehr exit and carried to the test laboratory in a heated oven so that the bottles were maintained at the lehr end temperature prior to application of the aqueous polymer mixture in accordance with the present invention. During transportation of the bottles from the lehr exit to the laboratory the bottles were maintained at a minimum temperature of 120° C.

EXAMPLE 1

A sample of 31 bottles was taken for testing, 16 were retained as untreated controls and 15 were dip coated by dipping into the aqueous emulsion.

The 16 untreated controls were found to burst at internal pressures ranging from 126 psi to 426 psi, the average bursting pressure of the 16 untreated bottles being 295 psi.

One of the dip-coated bottles was observed to have a contaminated surface. This bottle burst at a low pressure of 217 psi and was excluded from the average results. The remaining 14 dip-coated bottles which had a cured polymer coating in accordance with the present invention burst at internal pressures ranging from 283 psi to 513 psi, the average bursting pressure of the 14 treated bottles being 381 psi, an increase of 29% as compared with the average bursting pressure of the 16 untreated bottles.

EXAMPLE 2

A sample of 34 bottles was taken for testing, 20 being retained as untreated controls and 14 being spray-coated with the aqueous emulsion.

When the untreated bottles were tested for internal pressure strength, one bottle burst at 235 psi and one remained unbroken at an internal pressure of 551 psi. The average bursting pressure of the 20 untreated bottles was calculated at 410 psi, including 551 as the bursting pressure for the bottle which was unbroken at that pressure.

The 14 spray-coated bottles were subjected to similar tests up to internal pressures of 590 psi at which 5 bottles remained unbroken. The first of the spray-coated bottles to burst broke at 349 psi and the average bursting pressure of the 14 spray-coated bottles was 507 psi, an increase of 24% as compared with the average bursting pressure of the 20 untreated bottles.

The bottles used in the following Examples 3 to 7 were all newly-manufactured 275 ml bottles but in each of these examples the bottles were carried from the lehr exit in cartons during which time the bottles cooled. In the laboratory the bottles were re-heated in an oven prior to coating so that the bottles were at 105° C. when the aqueous emulsion coating was applied in accordance with the present invention.

EXAMPLE 3

In this Example a test was made to see whether there was any signifcant change in the effectiveness of the coating when the coating was freshly prepared as compared with a mix prepared two days previously.

A sample of 38 bottles was taken for testing, all of the bottles being coated by dipping.

Eighteen bottles were coated by dipping in a two-day old resin mix and the remaining twenty in a newly prepared resin mix of identical composition.

One of the bottles coated with the old resin mix burst at a very low pressure of 142 psi as a result of a "stone" in the shoulder of the bottle. This bottle was therefore excluded from the average results. The remaining 17 bottles were subjected to internal bursting pressure tests up to 590 psi at which three bottles remained unbroken. One bottle burst at a pressure of 254 psi and the average bursting pressure of the 17 bottles was 480 psi.

When the 20 bottles coated with the new resin mix were tested up to an internal bursting pressure of 590 psi, six bottles remained unbroken. One bottle burst at 294 psi and the average bursting pressure of the 20 bottles treated with the new resin mix was 490 psi, an increase of only 2% as compared with the 17 bottles coated with the two-day old resin mix, showing that the emulsion has a reasonable shelf life.

It was concluded that the effectiveness of the mix did not deteriorate when the mix was not immediately applied to the bottle.

Examples 4 to 6 were designed to test the effectiveness of the aqueous polymer systems according to the present invention in restoring strength to damaged bottles.

EXAMPLE 4

A sample of 50 bottles was taken, ten being retained as untreated controls and the remaining 40 bottles being hand scribed uniformly to trace a 1" (25 mm) long vertical scratch on the lower side wall about one third up from the bottle base.

Of these 40 scratched bottles 20 were tested without further treatment and the remaining 20 were then dip coated.

When subjected to the internal burst pressure test, the ten untreated, undamaged bottles burst in a range from 200 psi to 700 psi, the average bursting pressure being 490 psi.

Of the 20 untreated scratched bottles two broke at an internal pressure of about 100 psi, the strongest bottle at 400 psi, and the average bursting pressure was 198 psi.

The 20 damaged bottles which were treated in accordance with the present invention were found to burst at internal pressures ranging from 125 psi to 650 psi, the average bursting pressure of the 20 bottles being 400 psi. This is an increase of 102% on the average bursting pressure of the damaged but untreated bottles.

It was noted that four of the damaged but treated bottles burst at a point different from the place where the bottles had been damaged by the scribe mark.

It was further observed that, of the 20 untreated damaged bottles, four also burst at a point different from the scribe mark but three of these bottles were those which burst at the lower pressure in a range from below 100 psi to 125 psi.

It was deduced from the tests of this example that the aqueous polymer system of the present invention is effective in strengthening bottles which contain a flaw which would otherwise result in the bottle bursting relatively easily.

EXAMPLE 5

A sample of 46 bottles was taken for testing, ten bottles being retained as manufactured controls. All the remaining 36 bottles were indented using a standard Vickers diamond hardness (tester) indentor under a 10 kg load applied to the lower side wall about one third up from the bottle base. Sixteen of these indented bottles were retained as untreated controls and the remaining twenty were coated with the aqueous emulsion by mechanical dipping.

The ten manufactured controls, when subjected to internal bursting pressure tests, were found to burst in a range from 200 psi to 700 psi, the average bursting pressure being 490 psi.

When the 16 indented uncoated bottles were subjected to the internal bursting pressure test they burst in a range from 175 psi (one bottle) to 275 psi (two bottles). The average bursting pressure of the 16 indented uncoated bottles was 238 psi, less than half the pressure of the undamaged bottles. The average bursting pressure of the indented uncoated bottles which broke at the indent mark was 233 psi, only one bottle breaking at the shoulder rather than at the indent mark.

Of the 20 bottles which were indented and then treated according to the present invention, two burst at 275 psi, one burst at 600 psi and the average bursting pressure of the 20 bottles was 361 psi, an increase of 52% on the bursting pressure of the damaged but uncoated bottles.

Of the 20 indented but coated bottles, all but 3 broke at the indent mark.

EXAMPLE 6

A sample of 37 bottles was taken for testing, ten as manufactured controls and the remaining 27 being indented as in Example 5 under a 10 kg load on the lower side wall about one third up from the bottle base. Of the 27 indented bottles ten bottles were kept as untreated controls and 17 were dipcoated with aqueous emulsion. The first ten bottles which were dip-coated were dip-coated with the aqueous emulsion having a composition as described above, ie 482 grams of resin/silane mixture in 1.1 liters of water. The final seven bottles which were dip-coated were dipcoated with aqueous emulsion which contained 50% more water for the same resin/silane mixture content.

The ten bottles which were undamaged manufactured controls were found to burst at internal pressures ranging from 350 psi (two bottles) to 550 psi (one bottle), the average bursting pressure of the ten manufactured, undamaged control bottles being 445 psi.

The ten indented uncoated bottles all burst at the indent mark and were found to burst at internal pressures ranging from 225 psi (two bottles) to 300 psi (one bottle), the average bursting pressure of the 10 uncoated indented bottles being 255 psi.

Of the 17 indented and coated bottles it was found that the ten bottles coated with the undiluted coating burst at pressures ranging from 275 psi (one bottle) to 400 psi (one bottle), the average bursting pressure being 340 psi, a 33% increase over the average bursting pressure of the indented uncoated bottles.

The seven indented bottles coated with the diluted coating burst at pressures ranging from 300 psi (one bottle) to 450 psi (three bottles), the average bursting pressure being 393 psi, a 54% increase over the average bursting pressure of the indented uncoated bottles.

EXAMPLE 7

A sample of 30 bottles was taken for testing, ten being retained as untreated controls and the remaining 20 being mechanically dip coated with the aqueous emulsion.

The ten untreated controls were found to burst at internal pressures ranging from 350 psi (two bottles) to 550 psi (one bottle), the average bursting pressure of the ten untreated bottles being 445 psi.

One of the dip-coated bottles burst at only 50 psi and was excluded from the average results. The remaining 19 dip-coated bottles were found to burst at internal pressures ranging from 400 psi (one bottle) to 850 psi, at which one dip coated bottle burst and another one was unbroken. Two other dip coated bottles were unbroken at 800 psi, and one further bottle was unbroken at 750 psi. One bottle only burst at 750 psi at a second attempt and another bottle only burst at 700 psi at the second attempt. The average bursting pressure of the 19 dip coated bottles was 682 psi, a 53% increase over the uncoated bottles.

The two components of the mixture of this invention—that is to say the silane ane the resin—are each stable compositions which may be supplied in separate containers for mixing together when the mixture is to be made into an aqueous dispersion for coating a glass surface. The silane component of the mixture is capable of being stored dry in the dark for substantial periods before use, for example for two months.

It has been found that by use of a method in accordance with the present invention glass bottles may be treated at a low temperature, less than 200° C., to provide a polymeric coating which both strengthens and protects the bottle, which is strongly bonded to the glass surface in the form of a film, and which has a good surface finish and optical properties. The surface coating has been found to be a strong enduring coating resistant to mechanical abrasion and moisture attack.

According to another aspect of the present invention the ability to strengthen glass using a silane coupling agent in conjunction with a polymerisable resin as an aqueous emulsion is facilitated by the step of dissolving the silane in the resin as a preliminary step before bringing the resin and the water together to create the aqueous emulsion. The step of dissolving the silane in the resin has the effect that, when the aqueous emulsion has been formed, the water has to diffuse into the resin-silane droplets in order to make contact with the silane. Diffusion processes in polymeric meterials such as epoxy resins are slow processes with the result that reaction between the dissolved silane and the water occurs in a controlled fashion. Accordingly, the aqueous emulsion so formed can be applied to the surface of a glass article, for example a glass container, as described above, and the coating cured.

We claim:

1. A method of strengthening glass by applying to a surface of the glass a coating of a mixture of a silane and a resin containing at least two polymerisable unsaturated groups in the molecule, the resin being a reaction product of an epoxy resin with an unsaturated carboxylic acid, and then curing the coating, wherein the silane is a reaction product of a silane coupling agent, which contains an epoxy group, with an at least stoichiometric quantity of an unsaturated carboxylic acid reacting with said epoxy group, wherein the silane has an unsaturated reactive group with a reactivity similar to the reactivity of the polymerisable groups of the resin, and the mixture of the silane and the resin is applied to the surface of the glass as an aqueous emulsion; wherein, during curing, the silane and the resin form a covalently coupled interpenetrating network.

2. A method according to claim 1 wherein the silane coupling agent includes an organofunctional group containing a substituent epoxy group.

3. A method according to claim 1 wherein the silane coupling agent includes an ether linkage.

4. A method according to claim 1 wherein the silane coupling agent is a trialkoxyl silane having an alkyl chain containing a substituent epoxy group.

5. A method according to claim 1 wherein the substituent epoxy group is a terminal epoxy group.

6. A method according to claim 1 wherein the silane is a reaction product of the silane coupling agent with an acid of the formula

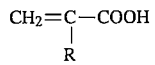

where R is hydrogen or an alkyl group.

7. A method according to claim 1 wherein the silane is a reaction product of the silane coupling agent with an unsaturated dibasic acid.

8. A method according to claim 1 wherein the resin is a reaction product of an epoxy resin with an acid of the formula

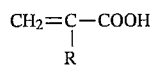

where R is hydrogen or an alkyl group.

9. A method according to claim 1 wherein the resin is a reaction product of an epoxy resin with a dibasic acid.

10. A method according to claim 1 wherein the silane is a reaction product of the silane coupling agent with acrylic acid, and the resin is an epoxy resin modified by the inclusion of acrylic acid residues.

11. A method according to claim 1 wherein the silane is a reaction product of the silane coupling agent with methacrylic acid, and the resin is an epoxy resin modified by the inclusion of methacrylic acid residues.

12. A method according to claim 1 wherein the mixture comprises at least 10 parts of the silane per 100 parts of the resin.

13. A method according to claim 12 wherein the mixture comprises from 15 to 30 parts of the silane per 100 parts of the resin.

14. A method according to claim 1 wherein the silane is dissolved in the resin and the resultant mixture is added to water and emulsified therein.

15. A method according to claim 1 wherein a glass container is strengthened by dipping the glass container in the aqueous emulsion.

16. A method according to claim 1 wherein a glass container is strengthened by spraying the outer surface of the glass container with the aqueous emulsion.

17. A method according to claim 1 wherein the resin is a heat-curable resin and the mixture further includes a free radical initiator.

18. A method according to claim 1, wherein the resin is based on a fluorinated bisphenol of formula

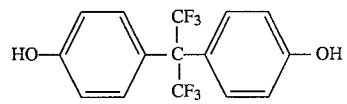

19. A method of strengthening a glass container by applying to an outer surface of the glass container an aqueous emulsion coating comprising a mixture of an acrylic-modified epoxy resin containing at least two polymerisable unsaturated groups in the molecule and a silane which is a reaction product of an epoxytrialkoxyl silane with an unsaturated carboxylic acid, the silane being present in an amount from 5 to 40 parts per hundred of the resin, and curing the coating.

20. A method according to claim 19 wherein the acrylic-modified epoxy resin includes a polymerisable diluent.

21. A method according to claim 20 wherein the polymerisable diluent is a diluent containing an acrylate substituent.

22. A method according to claim 19 wherein the unsaturated carboxylic acid is an acid of the formula

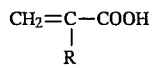

where R is hydrogen or an alkyl group.

23. A method according to claim 20 wherein the mixture comprises from 15 to 25 parts of the silane per hundred parts of the resin.

24. A method according to claim 20 wherein the mixture comprises about 20 parts of the silane per hundred parts of the resin.

25. A method according to claim 20 wherein the mixture further includes a surface active agent and the mixture is formed into an aqueous emulsion in a ratio of from 100 to 600 parts by weight of the mixture to 1,000 parts of water.

26. A method according to claim 20 wherein the glass container is strengthened by dipping the glass container in the aqueous emulsion which contains an amount of the order of 250 to 450 parts by weight of the mixture to 1,000 parts by weight of water.

27. A method according to claim 20 wherein the glass container is strengthened by spraying the outer surface of the glass container with the aqueous emulsion which contains an amount of the order of 150 to 200 parts by weight of the mixture to 1,000 parts by weight of water.

28. A method according to claim 20 wherein the resin and the silane are both reaction products of the same unsaturated carboxylic acid.

29. A method according to claim 1 wherein the resin is curable by irradiation with ultra-violet light.

30. A method according to claim 29 wherein the mixture further includes a photo initiator.

31. A method according to claim 30 wherein, after application of the aqueous emulsion to the surface of the glass, a period of time is allowed for evaporation of water before ultra violet irradiation is commenced.

32. A method according to claim 30 wherein after application of the aqueous emulsion to the surface of the glass a period of time is allowed for evaporation of water and pre-reaction between the uncured coating and the glass before ultra violet irradiation is commenced.

33. A method according to claim 32 wherein evaporation of water from the aqueous emulsion is facilitated by residual heat in the glass.

34. A method according to claim 32 wherein there is an application of heat to the glass during at least part of the said period of time.

35. A method according claim 1 wherein the mixture includes a plurality of silanes, each of which is a reaction product of a silane coupling agent which includes a substituent epoxy group with an unsaturated carboxylic acid.

36. A method according to claim 1 wherein the resin is based on bisphenol-A of formula

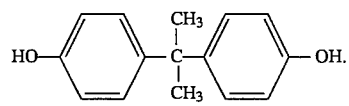

37. A method according to claim 1 wherein the resin is at least partly fluorinated.

38. A method according to claim 1 wherein the glass surface to which the aqueous emulsion is applied is first exposed to contact with water vapour.

39. A method according to claim 1 wherein the outer surface of the glass container is exposed to contact with water vapour during passage of the glass container through an annealing lehr before the aqueous emulsion is applied to the outer surface of the glass container.

40. A method according to claim 39 wherein additional water vapour is introduced into the annealing lehr.

* * * * *